US009739727B2

(12) United States Patent
Safai et al.

(10) Patent No.: US 9,739,727 B2
(45) Date of Patent: Aug. 22, 2017

(54) SYSTEMS AND METHODS FOR ALIGNING AN APERTURE

(71) Applicant: THE BOEING COMPANY, Huntington Beach, CA (US)

(72) Inventors: Morteza Safai, Newcastle, WA (US); Gary E. Georgeson, Tacoma, WA (US)

(73) Assignee: THE BOEING COMPANY, Chicago, IL (US)

( * ) Notice: Subject to any disclaimer, the term of this patent is extended or adjusted under 35 U.S.C. 154(b) by 81 days.

(21) Appl. No.: 14/601,277

(22) Filed: Jan. 21, 2015

(65) Prior Publication Data
US 2016/0209339 A1 Jul. 21, 2016

(51) Int. Cl.
G01N 23/203 (2006.01)

(52) U.S. Cl.
CPC ..... *G01N 23/203* (2013.01); *G01N 2223/053* (2013.01)

(58) Field of Classification Search
CPC ............... H01J 35/025; G01N 23/203; G01N 2223/053; H05G 1/26
See application file for complete search history.

(56) References Cited

U.S. PATENT DOCUMENTS

| 3,928,765 A * | 12/1975 | Teller ................... G01N 23/203 378/143 |
| 4,905,268 A | 2/1990 | Mattson et al. |
| 5,164,976 A * | 11/1992 | Scheid ................... A61B 6/502 378/146 |
| 5,550,886 A * | 8/1996 | Dobbs ................... A61B 6/032 378/19 |
| 6,157,703 A | 12/2000 | Solomon et al. |
| 6,370,218 B1 * | 4/2002 | Toth ....................... A61B 6/032 378/113 |
| 7,270,478 B2 | 9/2007 | Jimarez |
| 7,386,098 B2 | 6/2008 | Kanack et al. |
| 7,463,714 B2 | 12/2008 | Edwards et al. |
| 7,508,910 B2 | 3/2009 | Safai et al. |
| 7,529,343 B2 | 5/2009 | Safai et al. |
| 7,599,471 B2 | 10/2009 | Safai et al. |
| 7,623,626 B2 | 11/2009 | Safai et al. |
| 7,649,976 B2 | 1/2010 | Georgeson et al. |
| 7,738,630 B2 | 6/2010 | Burdett, Jr. et al. |
| 8,033,724 B2 | 10/2011 | Edwards et al. |
| 8,094,781 B1 | 1/2012 | Safai et al. |
| 8,761,338 B2 | 6/2014 | Safai |
| 9,295,434 B2 * | 3/2016 | Herold .................. A61B 6/032 |
| 2008/0037707 A1 * | 2/2008 | Rothschild .......... G01N 23/046 378/57 |
| 2013/0272497 A1 | 10/2013 | Goto et al. |
| 2014/0233697 A1 * | 8/2014 | Ignatyev ................ A61B 6/484 378/36 |
| 2015/0247946 A1 * | 9/2015 | Garretson ............ G01N 23/203 378/87 |
| 2015/0319832 A1 * | 11/2015 | Grimshaw ............... H05G 1/26 378/86 |

* cited by examiner

Primary Examiner — Wyatt Stoffa
(74) Attorney, Agent, or Firm — Armstrong Teasdale LLP

(57) ABSTRACT

An alignment system for aligning apertures in an X-ray backscatter system is provided. Additionally, a method for aligning apertures in an X-ray backscatter system is provided. Further, a computer-readable storage device including computer-executable instructions for aligning apertures in an X-ray backscatter system is provided.

20 Claims, 10 Drawing Sheets

SYSTEMS AND METHODS FOR ALIGNING AN APERTURE

BACKGROUND

The present disclosure relates generally to X-ray backscatter systems, and more particularly to aligning apertures of an X-ray backscatter system to improve the quality of images produced by the X-ray backscatter system.

Known X-ray backscatter systems tend to produce images with vertical streaking. The vertical streaking is caused by differences in the alignments of apertures in the X-ray backscatter system, resulting in diminished and inconsistent flux output (flux intensity) from the apertures. Precision in alignment and hole diameter improve the flux intensity of an aperture, but such precision is difficult to produce by fabrication and assembly alone. Painstaking manual trial and error adjustments are time consuming and rarely result in an optimum image. The result is reduced accuracy and precision in the images generated by the X-ray backscatter systems. Accordingly, in known systems, one option is to leave the apertures as they are, which saves time, but produces streaked images. A second option for known systems is to replace the apertures. The second option requires significant time to check the apertures and replace them and the streaking is usually only reduced to a relatively small degree. Additionally, over time, the streaking can increase due to mechanical misalignment and heating. Accordingly, it would be beneficial to have a system that automatically aligns apertures in an X-ray backscatter system without the need for manual trial and error.

BRIEF DESCRIPTION

In one aspect, an alignment system for aligning apertures in an X-ray backscatter system is provided. The alignment system includes an X-ray detector, a pair of motors, and a radiation flux analyzer device coupled to the X-ray detector and the pair of motors. The flux analyzer device is configured to operate the pair of motors to move an aperture to a plurality of different positions, receive signals from the X-ray detector at each of the plurality of positions, identify which aperture position exhibits the largest flux intensity based on the received signals, and operate the pair of motors to position the aperture at the identified position.

In another aspect, a method for aligning apertures in an X-ray backscatter system is provided. The method is performed using an alignment system that includes an X-ray detector, a pair of motors, and a radiation flux analyzer device coupled to the X-ray detector and the pair of motors. The method includes operating the pair of motors to move an aperture to a plurality of different positions, receiving signals from the X-ray detector at each of the plurality of positions, identifying which aperture position exhibits the largest flux intensity based on the received signals, and operating the pair of motors to position the aperture at the identified position.

In another aspect, a computer-readable storage device comprising computer-executable instructions for aligning apertures in an X-ray backscatter system is provided. When executed by a flux analyzer device included in an alignment system that includes an X-ray detector, a pair of motors, and the flux analyzer device coupled to the X-ray detector and the pair of motors, the computer-executable instructions cause the flux analyzer device to operate the pair of motors to move an aperture to a plurality of different positions, receive signals from the X-ray detector at each of the plurality of positions, identify which aperture position exhibits the largest flux intensity based on the received signals, and operate the pair of motors to position the aperture at the identified position.

DETAILED DESCRIPTION

Figure 1:
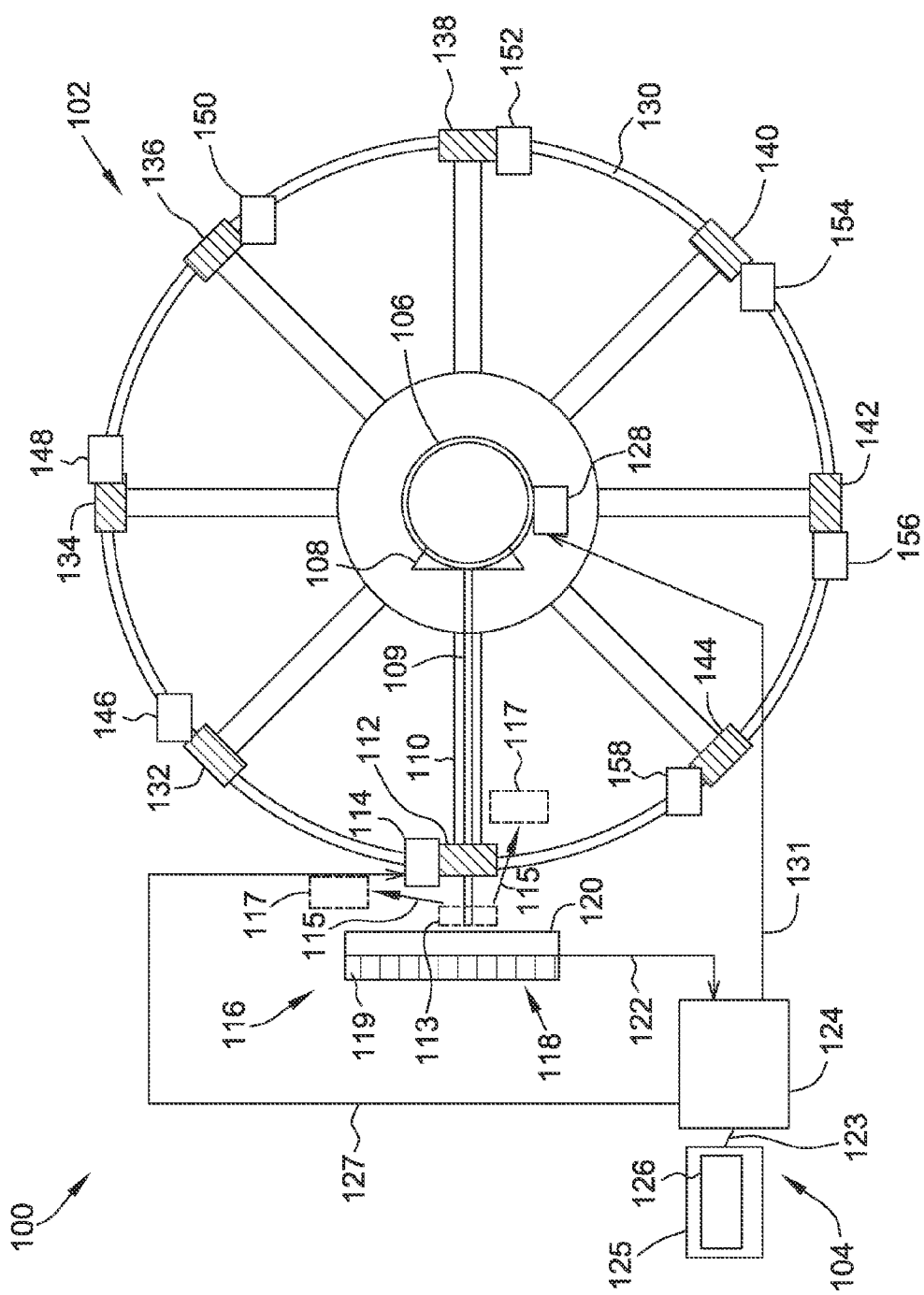
FIG. 1 is a diagram of an example environment including an X-ray backscatter system and an alignment system that includes a flux analyzer device.

FIG. 1 is a diagram of an example environment 100 including an X-ray backscatter system 102 and an alignment system 104. X-ray backscatter system 102 includes an X-ray source 106 that emits a cone beam 108. An X-ray beam 109 that is a portion of cone beam 108 enters a collimator tube 110, becomes collimated, and passes through an aperture 112. After passing through aperture 112, collimated X-ray beam 109 impinges on an object 113 to be inspected. A pair of imaging detectors 117 detect backscattered X-rays 115 from object 113. In at least some implementations, X-ray backscatter system 102 includes a plurality of apertures (e.g., apertures 112, 132, 134, 136, 138, 140, 156, and 158) mounted on a rotating wheel 130. In operation, the position of aperture 112 affects a flux intensity of X-ray beam 109. Inconsistencies in the intensities of X-ray beam 109 when emitted through the different apertures (e.g., apertures 112, 132, 134, 136, 138, 140, 156, and 158) may cause streaking in images generated by X-ray backscatter system 102.

Figure 2:
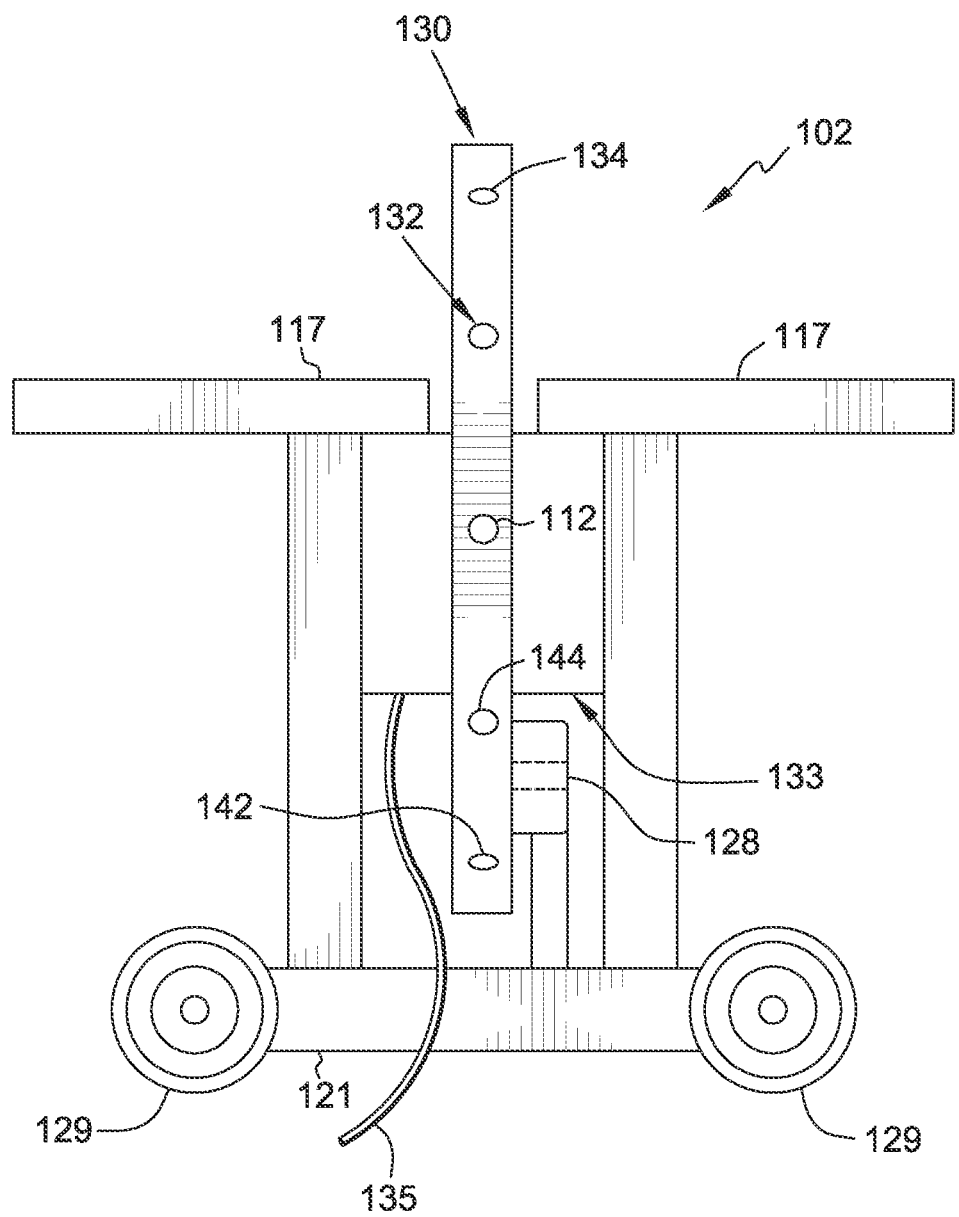
FIG. 2 is a side view of the X-ray backscatter system.

FIG. 2 is a side view of X-ray backscatter system 102. In at least some implementations, wheel 130 is coupled to a moveable platform 121. Movable platform 121 is supported by wheels 129. Additionally, moveable platform 121 is connected to a housing 133. Housing 133 is positioned within an interior of wheel 130. Housing 133 houses components (e.g., X-ray source 106) configured to generate X-rays (e.g., cone beam 108). Power is supplied to the components located inside of housing 133 through a power cable 135. A wheel motor 128 is configured to rotate wheel 130. In at least some implementations, wheel motor 128 rotates wheel 130 about 360 degrees. Detectors 117, which in at least some implementations are scintillator detectors, are configured to detect backscattered X-rays 115 (shown in FIG. 1) formed in response to X-ray beam 109 being reflected off of a surface (e.g., object 113).

Referring back to FIG. 1, when object 113 is not positioned to receive X-ray beam 109, alignment system 104 may be used to align the apertures of X-ray backscatter system 102. Alignment system 104 includes multiple pairs of alignment motors (e.g., alignment motor pairs 114, 146, 148, 150, 152, 154, 156, and 158), wherein each pair is configured to align or reposition a respective aperture (e.g., apertures 112, 132, 134, 136, 138, 140, 142, and 144) of X-ray backscatter system 102. Alignment system 104 additionally includes an alignment detector 116 that is positioned to receive X-ray beam 109 and facilitates aligning the apertures (e.g., apertures 112, 132, 134, 136, 138, 140, 142, and 144), as described herein. Alignment detector 116, in at least some implementations, includes an array 118 of detector elements 119. In at least some implementations, detector elements 119 are embodied as silicon elements or pixels. Alignment detector 116 is coupled to a scintillator 120. When X-ray beam 109 impinges scintillator 120, scintillator 120 emits photons in proportion to an intensity (i.e., flux intensity) of the X-ray beam 109 at each location on scintillator 120. One or more of the detector elements 119 receives the photons corresponding to the individual locations (i.e., pixels) of scintillator 120 excited by X-ray beam 109 and converts the photons to individual electrical signals. Alignment detector 116 transmits the electrical signals, referred to herein as detection signals 122, to a flux analyzer device 124. Flux analyzer device 124 determines a profile 300 of X-ray beam 109 from detection signals 122. More specifically, flux analyzer device 124 determines a flux intensity of X-ray beam 109 at each pixel of detector 116 based on a magnitude represented in the electrical signals for each pixel. The combined flux intensities for all of the detector elements 119 represent the flux intensity of the X-ray beam 109. In at least some implementations, flux analyzer device 124 includes or is coupled to a display device 125 and transmits an output signal 123 to display device 125 to present an output message 126 to a user. For example, in at least some implementations, output message 126 indicates that an aperture (e.g., first aperture 112) of X-ray backscatter system 102 should be replaced or re-machined.

Flux analyzer device 124 determines the flux intensity of X-ray beam 109, as described above, for a first position of first aperture 112. Next, flux analyzer device 124 transmits positioning signals 127 to first alignment motors 114 to move first aperture 112 on one or more of an X-axis, a Y-axis, and a Z-axis. By changing the positioning of first aperture 112, the flux intensity of X-ray beam 109 increases or decreases correspondingly. Flux analyzer device 124 determines the flux intensity of X-ray beam 109 for each position, then determines which one of the positions (the "peak flux position") generates a flux intensity (a "peak flux intensity") that is greater than any of the other flux intensities determined by flux analyzer device 124, for first aperture 112. After flux analyzer device 124 has determined the peak flux intensity and associated peak flux position, flux analyzer device 124 transmits positioning signals 127 to first alignment motors 114 to move first aperture 112 to the peak flux position. The positioning signals 127 transmitted by flux analyzer device 124 at this stage are referred to herein as alignment signals.

After determining the peak flux intensity and peak flux position for first aperture 112, and in at least some implementations, after transmitting the alignment signals to first alignment motors 114, flux analyzer device transmits an orientation signal 131 to a wheel motor 128 coupled to a wheel 130 of X-ray backscatter system 102. Orientation signal 131 causes wheel motor 128 to rotate wheel 130 from a first orientation, where X-ray beam 109 is emitted through first aperture 112, to a second orientation where a second aperture emits an X-ray beam from X-ray source 106 onto detector 116. More specifically, a plurality of apertures and associated alignment motors are positioned around wheel 130. Each aperture causes a different X-ray beam to be emitted from X-ray source 106 to detector 116. For example, first aperture 112 emits X-ray beam 109 having a first resolution and a second aperture 132 emits an X-ray beam from X-ray source 106 with a second resolution that is different from the first resolution. Flux analyzer device 124 determines a corresponding peak flux intensity and peak flux position for each aperture and transmits alignment signals to position each aperture in its respective peak flux position.

More specifically, in at least one implementation, wheel 130 includes first aperture 112, second aperture 132, a third aperture 134, a fourth aperture 136, a fifth aperture 138, a sixth aperture 140, a seventh aperture 142, and an eighth aperture 144. Additionally, first alignment motors 114 are coupled to first aperture 112, second alignment motors 146 are coupled to second aperture 132, third alignment motors 148 are coupled to third aperture 134, fourth alignment motors 150 are coupled to fourth aperture 136, fifth alignment motors 152 are coupled to fifth aperture 138, sixth alignment motors 154 are coupled to sixth aperture 140, seventh alignment motors 156 are coupled to seventh aperture 142, and eighth alignment motors 158 are coupled to eighth aperture 144 for moving each aperture to different positions, as described above with regard to first aperture 112 and first alignment motors 114. More specifically, flux analyzer device 124 determines a peak flux intensity and peak flux position for each of second aperture 132, third aperture 134, fourth aperture 136, fifth aperture 138, sixth aperture 140, seventh aperture 142, and eighth aperture 144 using the process described above, and transmits alignment signals to the corresponding alignment motors to position each aperture to its respective peak flux position.

Figure 3:
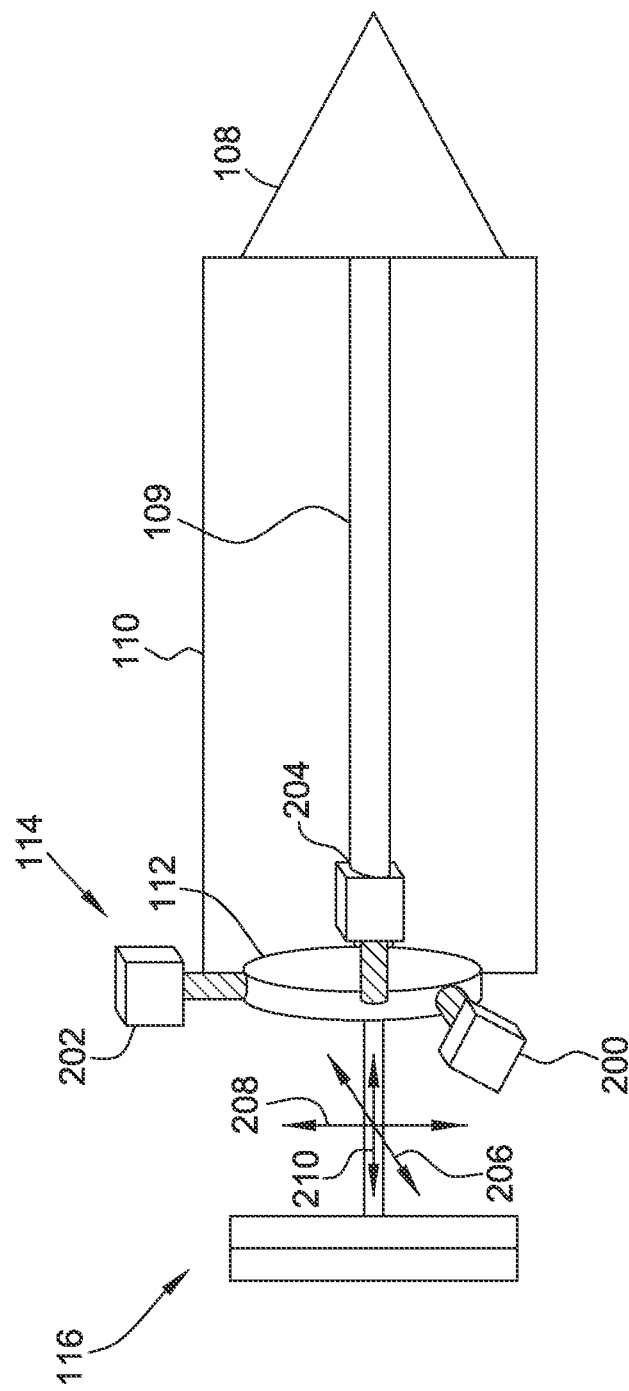
FIG. 3 is a diagram of alignment motors configured to position an aperture of the X-ray backscatter system.

FIG. 3 is a diagram of first alignment motors 114. First alignment motors 114 include a first motor 200, a second motor 202, and a third motor 204. First motor 200 is configured to position first aperture 112 on an X-axis 206. Second motor 202 is configured to position first aperture 112 on a Y-axis 208 that is perpendicular to X-axis 206. Third motor 204 is configured to position first aperture 112 on a Z-axis 210 that is perpendicular to X-axis 206 and to Y-axis 208. Each of second aperture 132, third aperture 134, fourth aperture 136, fifth aperture 138, sixth aperture 140, seventh aperture 142, and eighth aperture 144 and second alignment motors 146, third alignment motors 148, fourth alignment motors 150, fifth alignment motors 152, sixth alignment motors 154, seventh alignment motors 156, and eighth alignment motors 158 are configured correspondingly.

Figure 4:
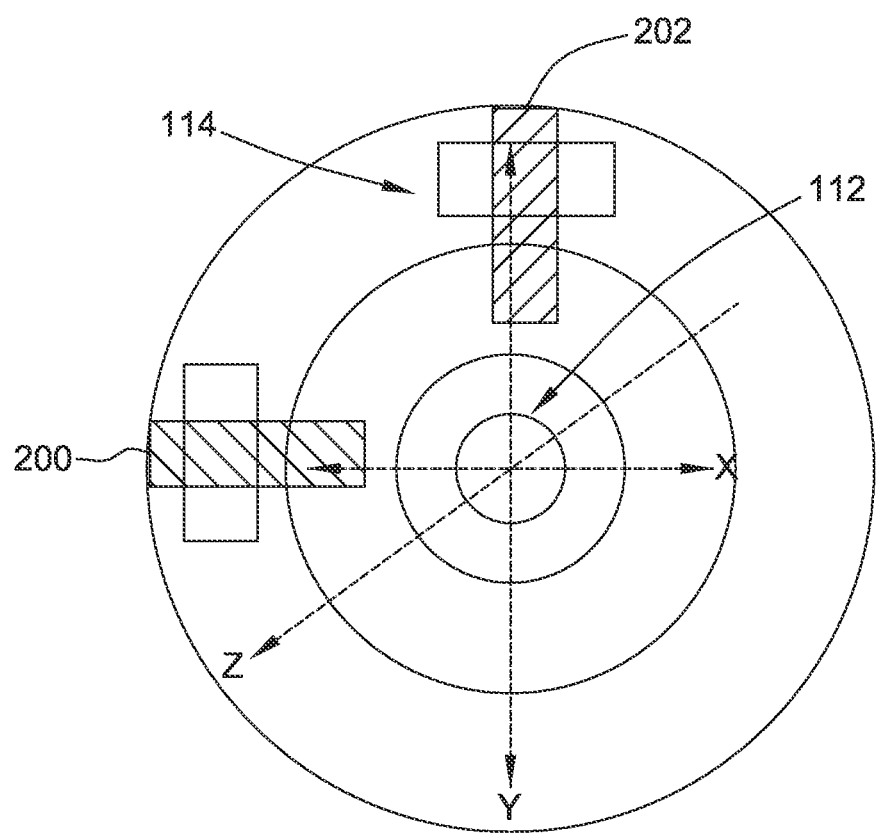
FIG. 4 is a diagram of an aperture of the X-ray backscatter system and corresponding alignment motors.

FIG. 4 is a diagram of aperture 112 of X-ray backscatter system 102 and corresponding alignment motors 114. X-axis motor 200 adjusts (e.g., translates) the position of aperture 112 along X-axis 206. Y-axis motor 202 adjusts (e.g., translates) the position of aperture 112 along Y-axis 208. Apertures 132, 134, 136, 138, 140, 142, 144 and corresponding motors 146, 148, 150, 152, 154, 156, and 158 are similarly configured. As described above, in some implementations, a Z-axis motor (e.g., Z-axis motor 204) adjusts the position of each aperture along Z-axis 210.

Figure 5:
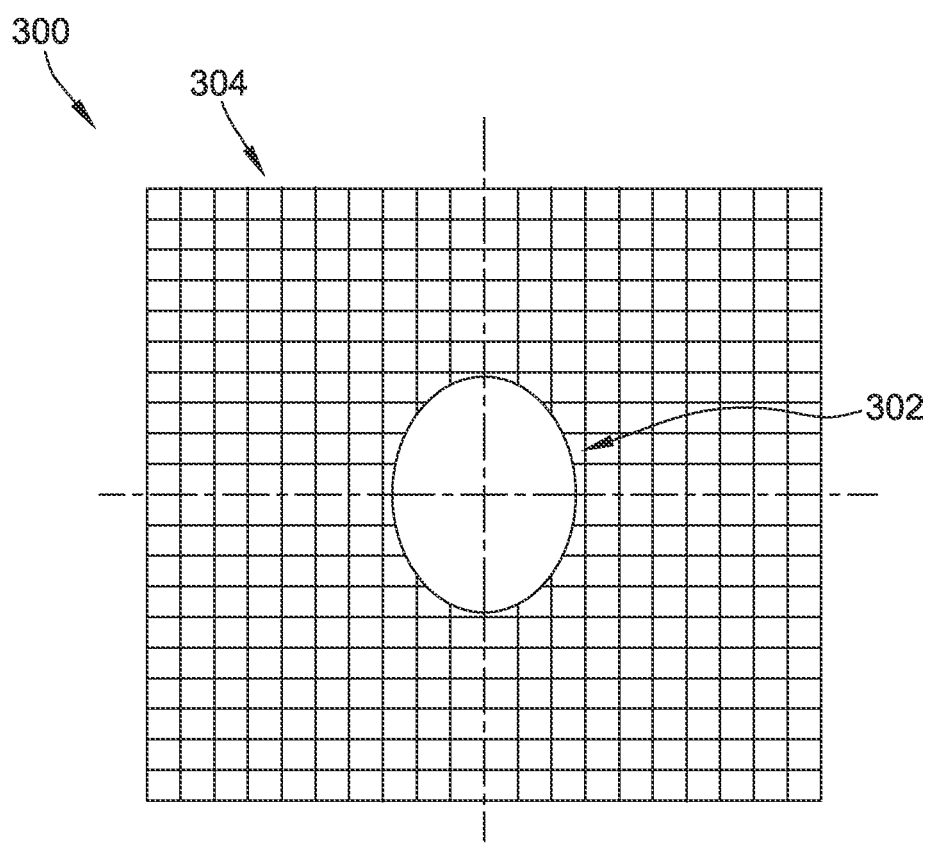
FIG. 5 is a profile of an X-ray beam emitted from the aperture of the X-ray backscatter system to a detector of the alignment system.

FIG. 5 is a profile 300 of an X-ray beam (e.g., X-ray beam 109) emitted from first aperture 112 of X-ray backscatter system 102 to detector 116 of alignment system 104. Beam profile 300 includes a plurality of pixels 304. A beam center 302 in profile 300 is an area of pixels 304 where X-ray beam 109 excites scintillator 120 of detector 116. As described above, detector 116 transmits detection signals 122 to flux analyzer device 124 with magnitudes (e.g., voltages) corresponding to flux intensities (e.g., proportional to an amount of excitation or photons emitted by scintillator 120) at each pixel 304. By combining the flux intensities at each pixel 304, flux analyzer device 124 determines a flux intensity of X-ray beam 109 for a given position of first aperture 112. As described above, flux analyzer device 124 determines a profile 300 and associated flux intensity for X-ray beam 109 for each of a plurality of positions for each aperture in X-ray backscatter system 102.

Figure 6:
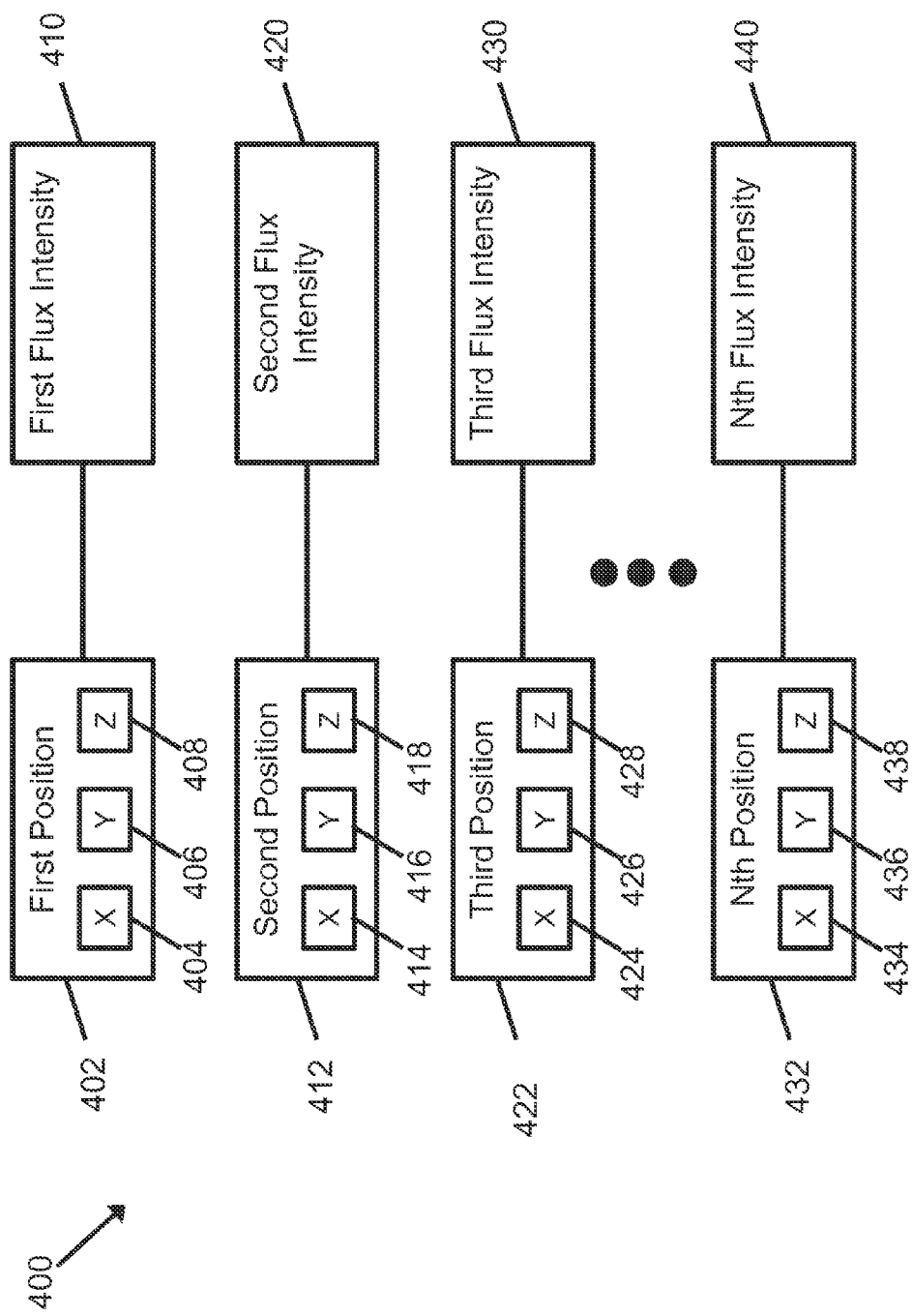
FIG. 6 is a diagram of a relationship between positions that the motors move the aperture to and flux intensities associated with each position.

FIG. 6 is a diagram of a relationship 400 between positions that first alignment motors 114 move first aperture 112 to, and flux intensities associated with each position. More specifically, flux analyzer device 124 transmits positioning signals 127 to first alignment motors 114 to position first aperture 112 on one or more of X-axis 206, Y-axis 208, and Z-axis 210 to a first position 402, having a corresponding first X component 404, a first Y component 406, and a first Z component 408. Next, flux analyzer device 124 determines a first flux intensity 410 associated with first position 402, as described above. Next, flux analyzer device 124 transmits positioning signals 127 to first alignment motors 114 to move first aperture 112 to a second position 412 having a second X component 414, a second Y component 416, and a second Z component 418. Next, flux analyzer device 124 determines a second flux intensity 420 associated with second position 412 of first aperture 112. Next flux analyzer device 124 transmits positioning signals 127 to first alignment motors 114 to move first aperture 112 to a third position 422 having a third X component 424, a third Y component 426, and a third Z component 428. Next flux analyzer device 124 determines a third flux intensity 430 associated with third position 422 of first aperture 112. Flux analyzer device 124 performs the above process for N positions of first aperture 112. Accordingly, flux analyzer device 124 transmits positioning signals 127 to first alignment motors 114 to move first aperture 112 to an Nth position 432 having an Nth X component 434, an Nth Y component 436, and an Nth Z component 438. Further, flux analyzer device 124 determines an Nth flux intensity 440 associated with Nth position 432.

In at least some implementations, N is a predefined number of positions, stored in a memory of flux analyzer device 124. In other implementations, N is determined by flux analyzer device 124 while iteratively determining flux intensities associated with each position of first aperture 112. More specifically, in at least some implementations, flux analyzer device 124 iteratively tests different positions until flux analyzer device 124 determines that one of the tested positions provides the peak flux intensity (i.e., all other tested and untested positions provide lower flux intensities). Flux analyzer device 124 performs the above process for every aperture of X-ray backscatter system 102.

Figure 7:
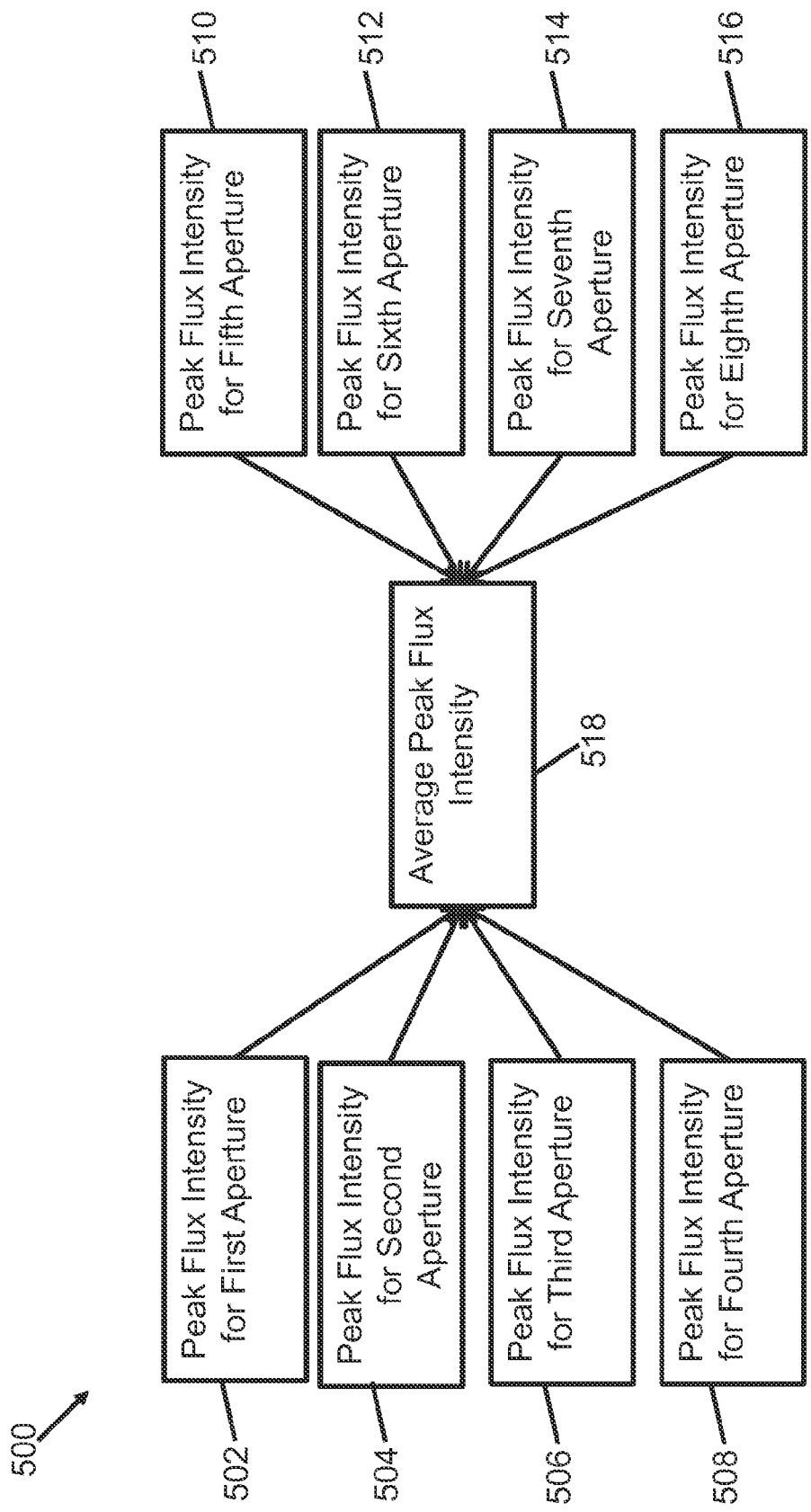
FIG. 7 is a diagram of a relationship between peak flux intensities of each of a plurality of apertures included in the X-ray backscatter system, and an average peak flux intensity determined by the flux analyzer device.

FIG. 7 is a diagram of a relationship 500 between peak flux intensities of each of the plurality of apertures included in X-ray backscatter system 102, and an average peak flux intensity 518 determined by flux analyzer device 124. More specifically, as described above, flux analyzer device 124 determines a first peak flux intensity 502 for first aperture 112, second peak flux intensity 504 for second aperture 132, a third peak flux intensity 506 for third aperture 134, a fourth peak flux intensity 508 for fourth aperture 136, a fifth peak flux intensity 510 for fifth aperture 138, a sixth peak flux intensity 512 for sixth aperture, a seventh peak flux intensity 514 for seventh aperture 142, and an eighth peak flux intensity 516 for eighth aperture 144. Additionally, flux analyzer device 124 determines average peak flux intensity 518 by averaging the peak flux intensities (e.g., peak flux intensities 502, 504, 506, 508, 510, 512, 514, and 516) associated with each aperture (e.g., apertures 112, 132, 134, 136, 138, 140, 142, and 144).

Figure 8:
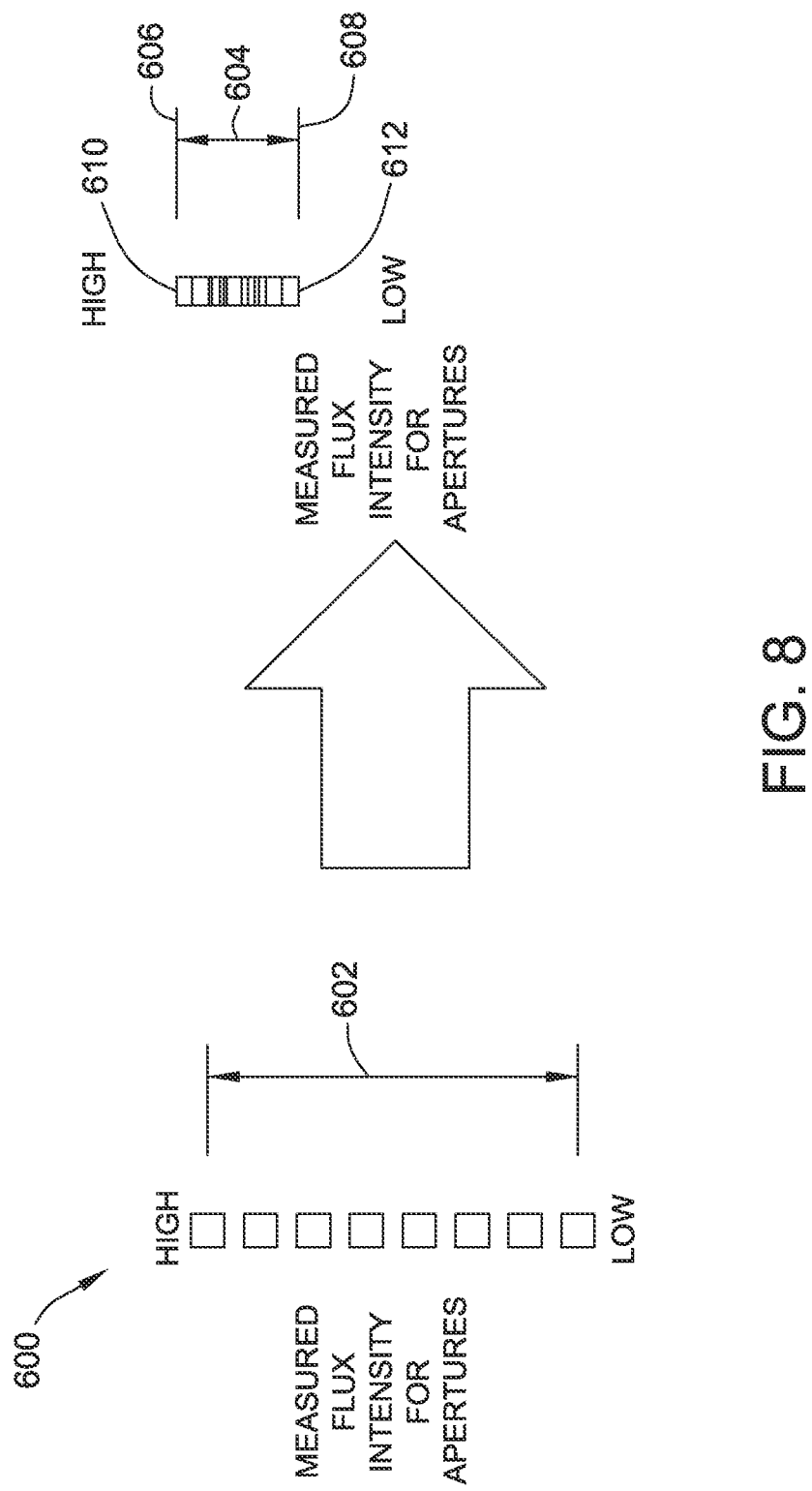
FIG. 8 is a diagram of a relationship between a first range of flux intensities before alignment, and a second range of flux intensities of the apertures after alignment by the alignment system.

FIG. 8 is a diagram of a relationship 600 between a first range 602 of flux intensities of the apertures (e.g., apertures 112, 132, 134, 136, 138, 140, 142, and 144) before alignment, and a second range 604 of flux intensities of the apertures (e.g., apertures 112, 132, 134, 136, 138, 140, 142, and 144) after alignment by alignment system 104. In first range 602, the flux intensities of the apertures may vary widely, as none of them have yet been aligned. After alignment system 104 aligns the apertures by the process described above, the flux intensities are peak flux intensities, for example peak flux intensities 502, 504, 506, 508, 510, 512, 514, and 516 (FIG. 5), and fall within a narrower range (e.g., second range 604). In at least some implementations, flux analyzer device 124 determines an upper intensity threshold 606 and a lower intensity threshold 608, such that any flux intensities greater than upper intensity threshold 606 (e.g., flux intensity 610) and any flux intensities less than lower intensity threshold 608 (e.g., flux intensity 612) require corrective action to bring the flux intensities within second range 604.

More specifically, if flux intensity 610 is, for example, first peak flux intensity 502, corresponding to Nth position 432 of first aperture 112, then flux analyzer device 124 transmits positioning signals 127 to first alignment motors 114 to move first aperture 112 to a different position (e.g., second position 412) having a lower flux intensity (e.g., second flux intensity 420) that is within second range 604. Further, if flux intensity 612 is, for example, second peak flux intensity 504, associated with second aperture 132, then second aperture 132 is re-machined or replaced. In some implementations, flux analyzer device 124 transmits an output signal 123 to display device 125 to display a message that second aperture 132 should be re-machined or replaced to increase the peak flux intensity of second aperture 132 to within second range 604. In at least some implementations, flux analyzer device 124 determines upper intensity threshold 606 and lower intensity threshold 608 as being plus or minus a percentage of average peak flux intensity 518, for example plus or minus two percent of average peak flux intensity 518.

Figure 9:
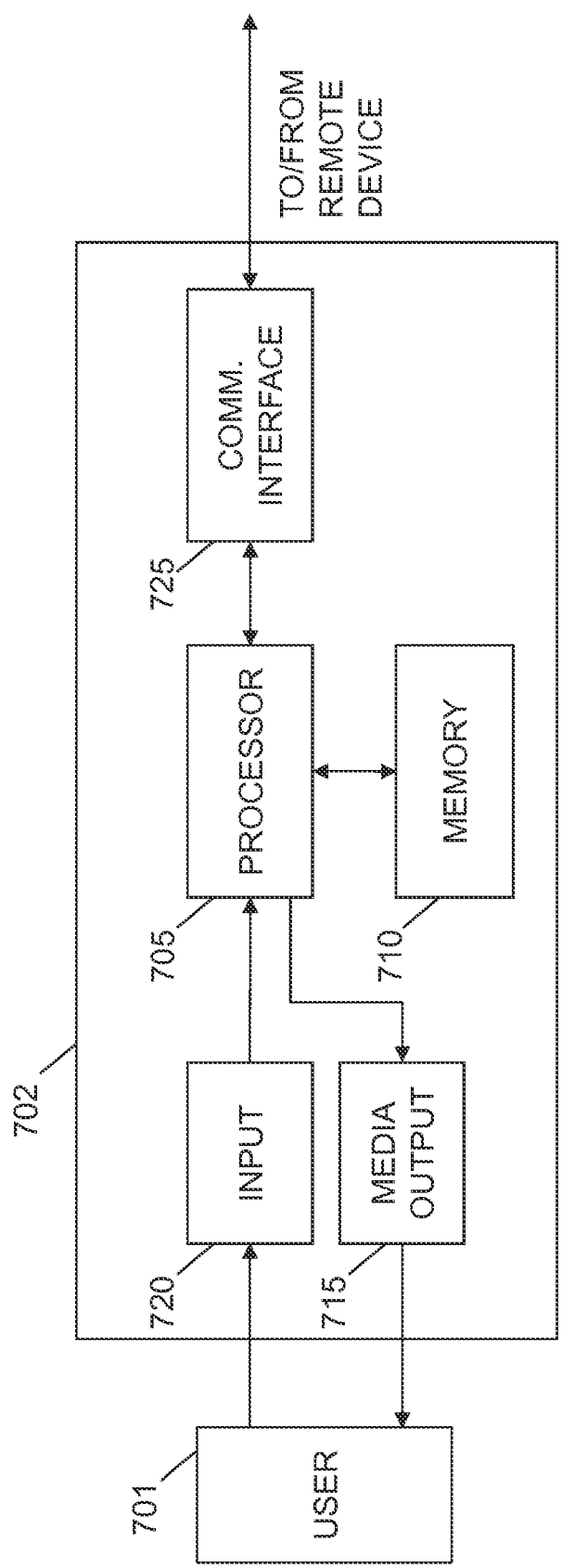
FIG. 9 is a diagram of an example computing device used in the environment of FIG. 1.

FIG. 9 is a diagram of an example computing device 702. Computing device 702 is representative of flux analyzer device 124. Computing device 702 includes one or more processors 705 for executing instructions. In some implementations, executable instructions are stored in a memory device 710. Processor 705 may include one or more processing units (e.g., in a multi-core configuration). One or more memory devices 710 are any one or more devices allowing information such as executable instructions and/or other data to be stored and retrieved. One or more memory devices 710 may include one or more computer-readable media.

Computing device 702 also includes at least one media output component 715 for presenting information to a user 701. Media output component 715 is any component capable of conveying information to user 701. In some implementations, media output component 715 includes an output adapter such as a video adapter and/or an audio adapter. An output adapter is operatively coupled to processor 705 and operatively couplable to an output device such as a display device (e.g., a liquid crystal display (LCD), organic light emitting diode (OLED) display, cathode ray tube (CRT), or "electronic ink" display) or an audio output device (e.g., a speaker or headphones).

In some implementations, computing device 702 includes an input device 720 for receiving input from user 701. Input device 720 may include, for example, a keyboard, a pointing device, a mouse, a stylus, a touch sensitive panel (e.g., a touch pad or a touch screen), a gyroscope, an accelerometer, a position detector, or an audio input device. A single component such as a touch screen may function as both an output device of media output component 715 and input device 720.

Computing device 702 additionally includes a communication interface 725, which is communicatively couplable to another device such as detector 116, alignment motors (e.g., first alignment motors 114, second alignment motors 146, third alignment motors 148, fourth alignment motors 150, fifth alignment motors 152, sixth alignment motors 154, seventh alignment motors 156, and eighth alignment motors 158), and wheel motor 128. Communication interface 725 may include, for example, a wired or wireless network adapter or a wireless data transceiver for use with a mobile phone network (e.g., Global System for Mobile communications (GSM), 3G, 4G or Bluetooth) or other mobile data network (e.g., Worldwide Interoperability for Microwave Access (WIMAX)).

Stored in one or more memory devices 710 are, for example, computer-readable instructions for providing a user interface to user 701 via media output component 715 and, optionally, receiving and processing input from input device 720. A user interface may include, text, graphics, and/or sound that enable user 701 to interact with computing device 702, for example to control operations of computing device 702 and/or view output (e.g., output message 126). The computer-readable instructions additionally cause computing device 702 perform the processes for aligning apertures of X-ray backscatter system 102 described above.

Figure 10:
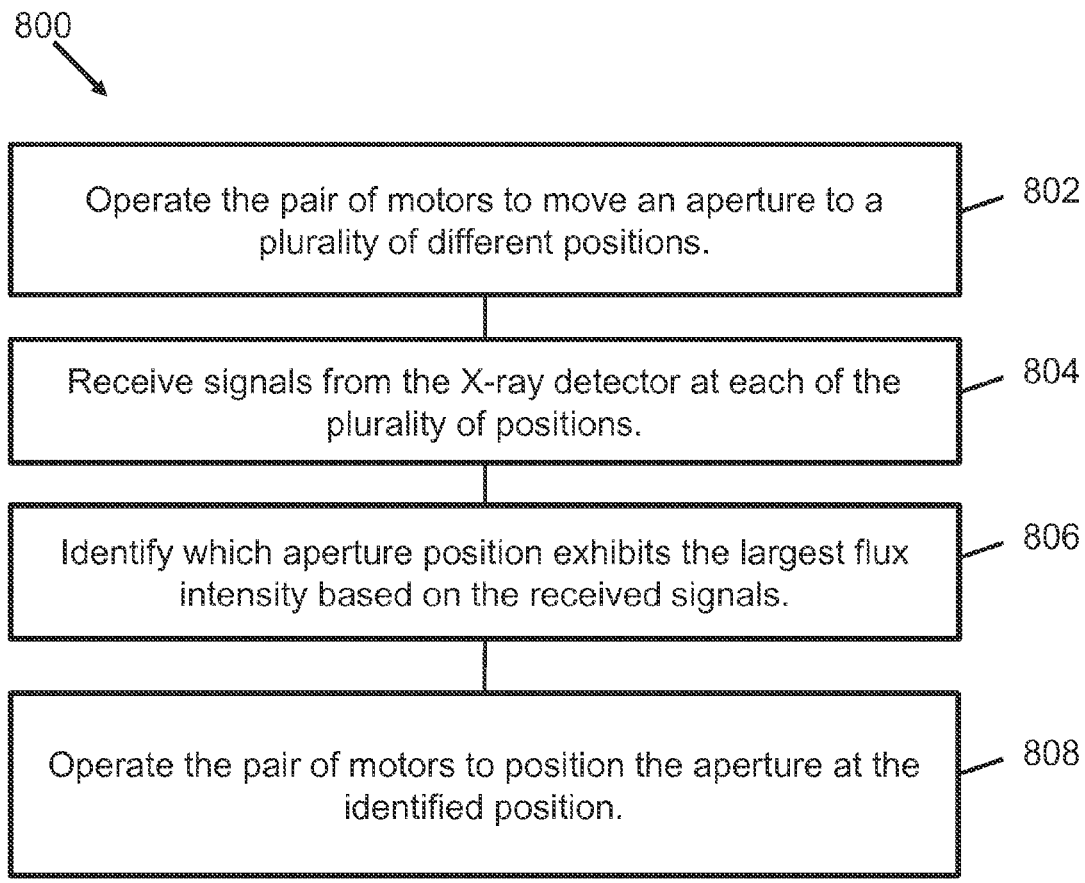
FIG. 10 is a flowchart of an example process for aligning apertures in the X-ray backscatter system of FIG. 1.

FIG. 10 is a flowchart of an example process 800 for aligning apertures in X-ray backscatter system 102. Initially, flux analyzer device 124 operates 802 a pair of motors (e.g., motors 114) to move an aperture (e.g., first aperture 112) to a plurality of different positions (e.g., first position 402, second position 412, third position 422, Nth position 432). Additionally, flux analyzer device 124 receives 804 signals (e.g., detection signals 122) from an X-ray detector (e.g., X-ray detector 116) at each of the plurality of positions. Additionally, flux analyzer device 124 identifies 806 which aperture position (e.g., first position 402, second position 412, third position 422, Nth position 432) exhibits the largest flux intensity (e.g., peak flux intensity 502) based on the received signals (e.g., detection signals 122). Additionally, flux analyzer device 124 operates 808 the pair of motors 114 to position the aperture (e.g., first aperture 112) at the identified position (e.g., one of first position 402 through Nth position 432).

In some implementations, flux analyzer device 124 determines a respective peak flux intensity and a respective peak flux position for each of the plurality of apertures (e.g., first aperture 112, second aperture 132, third aperture 134, fourth aperture 136, fifth aperture 138, sixth aperture 140, seventh aperture 142, and eighth aperture 144). In some implementations, flux analyzer device 124 determines an average peak flux intensity (e.g., average peak flux intensity 518) by averaging together the peak flux intensities (e.g., peak flux intensities 502, 504, 506, 508, 510, 512, 514, and 516) associated with each of the plurality of apertures (e.g., first aperture 112, second aperture 132, third aperture 134, fourth aperture 136, fifth aperture 138, sixth aperture 140, seventh aperture 142, and eighth aperture 144). Additionally, flux analyzer device 124 determines an acceptable intensity range (e.g., second range 604) by determining an upper intensity threshold (e.g., upper intensity threshold 606) that is a predefined percentage (e.g., two percent) greater than the average peak flux intensity (e.g., average peak flux intensity 518) and determines a lower intensity threshold (e.g., lower intensity threshold 608) that is the predefined percentage (e.g., two percent) less than the average peak flux intensity (e.g., average peak flux intensity 518).

In some implementations, flux analyzer device 124 determines that at least one of the plurality of apertures (e.g., first aperture 112) has a peak flux intensity (e.g., peak flux intensity 502) that is greater than the upper intensity threshold (e.g., upper intensity threshold 606) and transmits positioning signals (e.g., positioning signals 127) to at least one of the first motor (e.g., first motor 200) and the second motor (e.g., second motor 202) to move the at least one of the plurality of apertures (e.g., first aperture 112) to one of the plurality of positions (e.g., first position 402) that is associated with one of the plurality of flux intensities (e.g., first flux intensity 410) that is within the acceptable intensity range (e.g., second range 604).

In some implementations, flux analyzer device 124 determines that at least one of the plurality of apertures (e.g., second aperture 132) has a peak flux intensity (e.g., peak flux intensity 504) that is less than the lower intensity threshold (e.g., lower intensity threshold 608) and transmits an output signal (e.g., output signal 123) to an output device (e.g., display device 125) to display a message (e.g., output message 126) indicating that the at least one aperture (e.g., second aperture 132) having a peak flux intensity (e.g., peak flux intensity 504) less than the lower intensity threshold (e.g., lower intensity threshold 608) should be replaced or re-machined.

In some implementations, flux analyzer device 124 transmits positioning signals 127 to a third motor (e.g., third motor 204) to move the first aperture (e.g., first aperture 112) on a Z-axis (e.g., Z-axis 210) that is perpendicular to an X-axis (X-axis 206) and a Y-axis (e.g., Y-axis 208). In some implementations, flux analyzer device 124 transmits an orientation signal (e.g., orientation signal 131) to wheel motor 128 to rotate wheel 130 from a first orientation to a second orientation, wherein the second aperture (e.g., second aperture 132) emits X-rays onto the detector (e.g., detector 116).

A technical effect of systems and methods described herein includes at least one of: (a) operating a pair of motors to move an aperture to a plurality of different positions; (b) receiving signals from an X-ray detector at each of the plurality of positions; (c) identifying which aperture position exhibits the largest flux intensity based on the received signals; and (d) operating the pair of motors to position the aperture at the identified position.

As compared to known methods and systems for aligning the positioning of apertures in an X-ray backscatter system, the methods and systems described herein enable automated alignment of apertures. Accordingly, users of X-ray backscatter systems may obtain more precise and accurate images from an X-ray backscatter system without incurring the time and costs of manually aligning the apertures.

The description of the different advantageous implementations has been presented for purposes of illustration and description, and is not intended to be exhaustive or limited to the implementations in the form disclosed. Many modifications and variations will be apparent to those of ordinary skill in the art. Further, different advantageous implementations may provide different advantages as compared to other advantageous implementations. The implementation or implementations selected are chosen and described in order to best explain the principles of the implementations, the practical application, and to enable others of ordinary skill in the art to understand the disclosure for various implementations with various modifications as are suited to the particular use contemplated. This written description uses examples to disclose various implementations, which include the best mode, to enable any person skilled in the art to practice those implementations, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An alignment system for aligning apertures in an X-ray backscatter system that includes a backscatter X-ray detector, said alignment system comprising:
   an alignment detector configured to receive an X-ray beam through an aperture in the X-ray backscatter system;
   a pair of motors; and
   a radiation flux analyzer device coupled to the alignment detector and the pair of motors, said flux analyzer device is configured to:
      operate the pair of motors such that the aperture moves to a plurality of different positions;
      receive signals from the alignment detector at each of the plurality of different positions;
      identify which of the plurality of different positions exhibits a largest flux intensity based on the received signals; and
      operate the pair of motors to position the aperture at the identified position to mitigate streaking in images generated by the backscatter X-ray detector.

2. The alignment system of claim 1, wherein the alignment detector comprises an X-ray transmission detector.

3. The alignment system of claim 1, wherein the X-ray backscatter system further includes a plurality of apertures, and said flux analyzer device is further configured to determine a respective peak flux intensity and a respective peak flux position for each of the plurality of apertures.

4. The alignment system of claim 3, wherein said flux analyzer device is further configured to:
   determine an average peak flux intensity by averaging together the peak flux intensities associated with each of the plurality of apertures; and
   determine an acceptable intensity range by:
      determining an upper intensity threshold that is a predefined percentage greater than the average peak flux intensity; and
      determining a lower intensity threshold that is the predefined percentage less than the average peak flux intensity.

5. The alignment system of claim 4, wherein said flux analyzer device is further configured to:
   determine that at least one aperture of the plurality of apertures has a peak flux intensity that is greater than the upper intensity threshold; and
   position the at least one aperture of said plurality of apertures to one of the plurality of different positions that is associated with one of the plurality of flux intensities that is within the acceptable intensity range.

6. The alignment system of claim 4, wherein said flux analyzer device is coupled to an output device, said flux analyzer device is further configured to:
   determine that at least one aperture of the plurality of apertures has a peak flux intensity that is less than the lower intensity threshold; and
   transmit an output signal to said output device to display a message indicating that the at least one aperture having a peak flux intensity less than the lower intensity threshold should be replaced or re-machined.

7. The alignment system of claim 1, further comprising a third motor coupled to the aperture, wherein the third motor is configured to position a first aperture on a Z-axis that is perpendicular to an X-axis and a Y-axis.

8. The alignment system of claim 1, wherein the X-ray backscatter system further includes a wheel and a wheel motor coupled to the wheel, wherein the wheel includes at least the aperture and a second aperture, and wherein said flux analyzer device is further configured to transmit an orientation signal to the wheel motor to rotate the wheel from a first orientation to a second orientation, wherein the second aperture emits X-rays onto said alignment detector.

9. A method for aligning apertures in an X-ray backscatter system that includes a backscatter X-ray detector, said method is performed using an alignment system that includes an alignment detector configured to receive an X-ray beam through an aperture in the X-ray backscatter system, a pair of motors, and a radiation flux analyzer device coupled to the alignment detector and the pair of motors, said method comprising:
   operating the pair of motors such that the aperture moves to a plurality of different positions;
   receiving signals from the alignment detector at each of the plurality of different positions;
   identifying which of the plurality of different positions exhibits a largest flux intensity based on the received signals; and
   operating the pair of motors to position the aperture at the identified position to mitigate streaking in images generated by the backscatter X-ray detector.

10. The method of claim 9, wherein the X-ray backscatter system further includes a plurality of apertures, said method further comprising determining, by the flux analyzer device, a respective peak flux intensity and a respective peak flux position for each of the plurality of apertures.

11. The method of claim 10, further comprising:
   determining, by the flux analyzer device, an average peak flux intensity by averaging together the peak flux intensities associated with each of the plurality of apertures; and
   determining an acceptable intensity range by:
      determining an upper intensity threshold that is a predefined percentage greater than the average peak flux intensity; and
      determining a lower intensity threshold that is the predefined percentage less than the average peak flux intensity.

12. The method of claim 11, further comprising:
determining, by the flux analyzer device, that at least one aperture of the plurality of apertures has a peak flux intensity that is greater than the upper intensity threshold; and
positioning the at least one aperture of the plurality of apertures to one of the plurality of different positions that is associated with one of the plurality of flux intensities that is within the acceptable intensity range.

13. The method of claim 11, wherein the flux analyzer device is coupled to an output device, said method further comprising:
determining, by the flux analyzer device, that at least one aperture of the plurality of apertures has a peak flux intensity that is less than the lower intensity threshold; and
transmitting an output signal to the output device to display a message indicating that the at least one aperture having a peak flux intensity less than the lower intensity threshold should be replaced or re-machined.

14. The method of claim 9, wherein the alignment system further includes a third motor coupled to the aperture, said method further comprising positioning the aperture on a Z-axis that is perpendicular to an X-axis and a Y-axis, using the third motor.

15. The method of claim 9, wherein the X-ray backscatter system further includes a wheel, and the aperture is one of a plurality of apertures positioned around the wheel, said method further comprising:
after determining a peak flux intensity and a peak flux position of the aperture, rotating the wheel such that at least a second aperture of the plurality of apertures emits X-rays onto the alignment detector; and
determining a respective peak flux intensity and a respective peak flux position for the second aperture.

16. A non-transitory computer-readable storage device comprising computer-executable instructions for aligning apertures in an X-ray backscatter system that includes a backscatter X-ray detector, wherein, when executed by a flux analyzer device included in an alignment system that includes an alignment detector configured to receive an X-ray beam through an aperture in the X-ray backscatter system, a pair of motors, and the flux analyzer device coupled to the alignment detector and the pair of motors, said computer-executable instructions cause the flux analyzer device to:
operate the pair of motors such that the aperture moves to a plurality of different positions;
receive signals from the alignment detector at each of the plurality of different positions;
identify which of the plurality of different positions exhibits a largest flux intensity based on the received signals; and
operate the pair of motors to position the aperture at the identified position to mitigate streaking in images generated by the backscatter X-ray detector.

17. The non-transitory computer-readable storage device of claim 16, wherein the X-ray backscatter system further includes a plurality of apertures, said computer-executable instructions further cause the flux analyzer device to determine a respective peak flux intensity and a respective peak flux position for each of the plurality of apertures.

18. The non-transitory computer-readable storage device of claim 17, wherein said computer-executable instructions additionally cause the flux analyzer device to:
determine an average peak flux intensity by averaging together the peak flux intensities associated with each of the plurality of apertures; and
determine an acceptable intensity range by:
determining an upper intensity threshold that is a predefined percentage greater than the average peak flux intensity; and
determining a lower intensity threshold that is the predefined percentage less than the average peak flux intensity.

19. The non-transitory computer-readable storage device of claim 18, wherein said computer-executable instructions additionally cause the flux analyzer device to:
determine that at least one aperture of the plurality of a apertures has a peak flux intensity that is greater than the upper intensity threshold; and
move the at least one aperture of the plurality of apertures to one of the plurality of different positions that is associated with one of the plurality of flux intensities that is within the acceptable intensity range.

20. The non-transitory computer-readable storage device of claim 18, wherein the flux analyzer device is coupled to an output device, and wherein said computer-executable instructions further cause the flux analyzer device to:
determine that at least one aperture of the plurality of apertures has a peak flux intensity that is less than the lower intensity threshold; and
transmit an output signal to the output device to display a message indicating that the at least one aperture having a peak flux intensity less than the lower intensity threshold should be replaced or re-machined.

* * * * *